(12) United States Patent
Fenner et al.

(10) Patent No.: US 6,501,355 B2
(45) Date of Patent: Dec. 31, 2002

(54) SYSTEM HAVING A SWITCHING DEVICE AND AN EVALUATION DEVICE FOR DETERMINING A REMAINING SERVICE LIFE OF A CONTACT PIECE

(75) Inventors: Matthias Fenner, Wiesbaden (DE); Frank Berger, Swisttal-Miel (DE); Klaus-Jochen Froehlich, Dresden (DE); Bernd Koehler, Dresden (DE)

(73) Assignee: Moeller GmbH, Bonn (DE)

( * ) Notice: Subject to any disclaimer, the term of this patent is extended or adjusted under 35 U.S.C. 154(b) by 0 days.

(21) Appl. No.: 10/101,786

(22) Filed: Mar. 20, 2002

(65) Prior Publication Data

US 2002/0158728 A1 Oct. 31, 2002

Related U.S. Application Data

(63) Continuation of application No. PCT/EP00/08769, filed on Sep. 8, 2000.

(30) Foreign Application Priority Data

Sep. 20, 1999 (DE) .......................................... 199 45 059

(51) Int. Cl.[7] .............................. H01H 5/00; H01H 7/16; H01H 75/00; C21B 7/24
(52) U.S. Cl. .......................... 335/156; 73/584; 73/596; 73/627; 73/628
(58) Field of Search ............................. 335/156; 73/570, 73/584, 596, 627–629, 632

(56) References Cited

U.S. PATENT DOCUMENTS 6,313,636 B1 * 11/2001 Pohl et al. ................... 324/421

FOREIGN PATENT DOCUMENTS

| DE | 3714802 | 11/1988 |
|----|---------|---------|
| DE | 4440423 | 5/1996 |
| DE | 19523270 | 9/1996 |
| EP | 0333139 | 9/1989 |
| JP | 57151829 | 9/1982 |
| JP | 58156851 | 9/1983 |

* cited by examiner

Primary Examiner—Ramon M. Barrera
(74) Attorney, Agent, or Firm—Davidson, Davidson & Kappel, LLC

(57) ABSTRACT

A system includes a switching device, a sound device and an evaluation device. The switching device includes a housing and a contact system disposed in the housing, the contact system including a contact piece carrier and a contact piece disposed on the contact piece carrier. The sound device produces and captures structure-borne sound waves so as to determine an equivalent criterion for determining the remaining service life of the contact piece. The evaluation device evaluates the equivalent criterion.

15 Claims, 2 Drawing Sheets

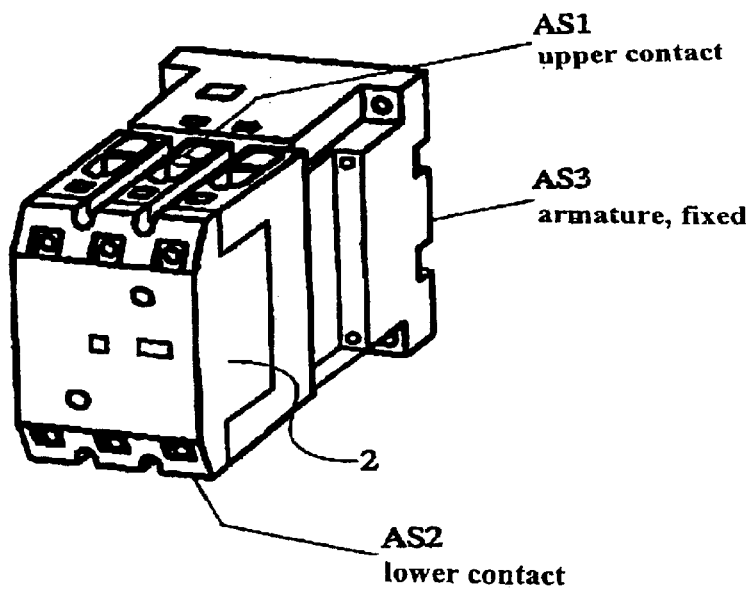
Fig. 1
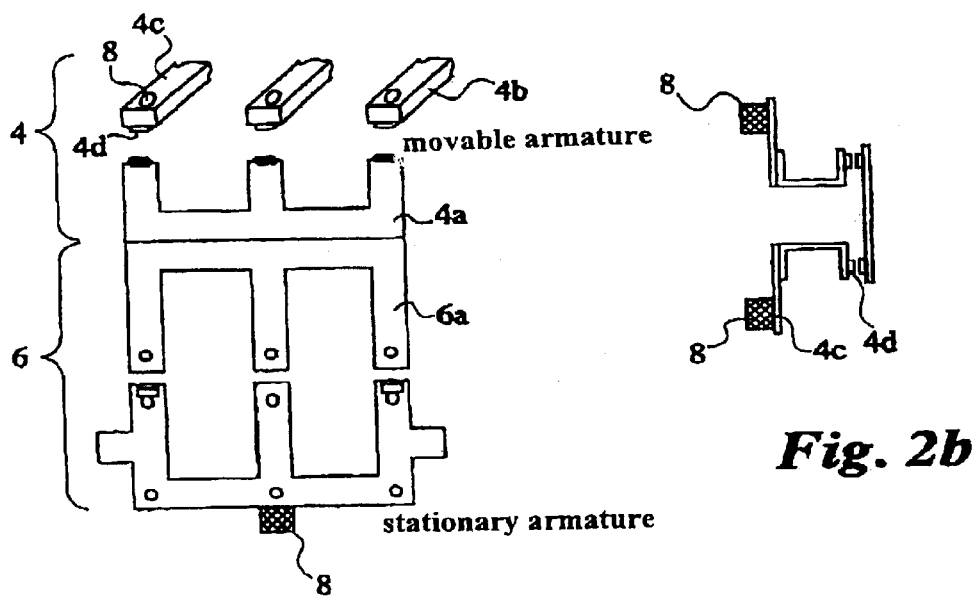
Fig. 2a
Fig. 2b

SYSTEM HAVING A SWITCHING DEVICE AND AN EVALUATION DEVICE FOR DETERMINING A REMAINING SERVICE LIFE OF A CONTACT PIECE

BACKGROUND

The present invention relates generally to switching devices and, in particular, to a system including a switching device and an evaluation device for determining a remaining service life of a contact piece of the switching device.

German Patent Application No. DE 37 14 802 A1 describes an electric switch in which contact erosion is monitored via an optical fiber system. In this context, a fiber optic guide is arranged between the end face of the contact piece to be monitored and the contact carrier assigned thereto, nearly parallel to the end face of the contact piece. Because of this, unacceptably high contact erosion results in the destruction of the fiber optic guide and thus, in the change of its optical properties. These changes are then evaluated so that the existence of a certain contact erosion can be detected at a stage where the contacts can still be expected to have a limited service life. In this context, however, erosion can actually be detected only upon the destruction of the fiber optic guide and thus, only after a certain wear of the contact piece. Moreover, the contact piece to be examined is predamaged by embedding a fiber optic guide so that the contact piece experiences a suddenly occurring increase in wear due to the opening in the material when it is eroded down to the level of the fiber optic guide.

SUMMARY OF THE INVENTION

An object of the present invention is to provide a system capable of evaluating, in a nearly wear-free manner and without predamaging the contact piece, contact piece wear at any arbitrary instant of the contact piece wear.

The present invention provides a system including a switching device, a sound device and an evaluation device. The switching device includes a housing and a contact system disposed in the housing, the contact system including a contact piece carrier and a contact piece disposed on the contact piece carrier. Th e sound device produces and captures structure-borne sound waves so as to determine an equivalent criterion useable for determining a remaining service life of the contact piece. The evaluation device evaluates the equivalent criterion.

Each state of wear of a contact piece is associated with specific characteristics thereof. Thus, as the wear increases, the contact piece changes its properties with respect to the transmission or reflection characteristics for sound waves passing through the contact piece. According to the present invention, these changes are detected by acoustic aids and evaluated in an evaluation device, thus determining a corresponding wear state. According to the present invention, acoustic aids are used which, on one hand, are capable of producing sound waves in a desired degree so that a defined injection of sound waves can be injected into the contact piece to be examined and which, on the other hand, are able to capture sound waves which occur in the contact piece.

Advantageously, a single acoustic aid in the form of a piezoelectric element may be used for producing and capturing the sound waves. These high-power piezoelectric elements can be arranged, in particular, in the form of thin layer elements on the contact piece carrier, preferably immediately opposite the contact piece to be examined, on the other side of the same contact piece carrier.

BRIEF DESCRIPTION OF THE DRAWINGS

Further details and advantages of the present invention will be explained based on an exemplary embodiment with reference to the drawings.

FIG. 1 shows a switching device according to the present invention in the form of a contactor.

FIG. 2a shows a schematic perspective representation of the magnetic drive and contact system of a switching device according to FIG. 1.

FIG. 2b shows a schematic lateral representation of the magnetic drive and contact system of a switching device according to FIG. 1.

DETAILED DESCRIPTION

Figure 3A:
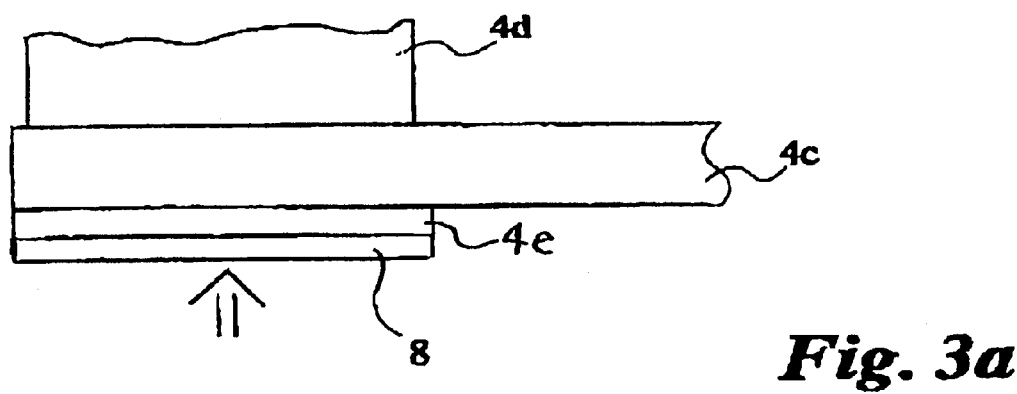
FIG. 3a is a lateral view of a switching contact featuring a piezoelectric element.
Figure 3B:
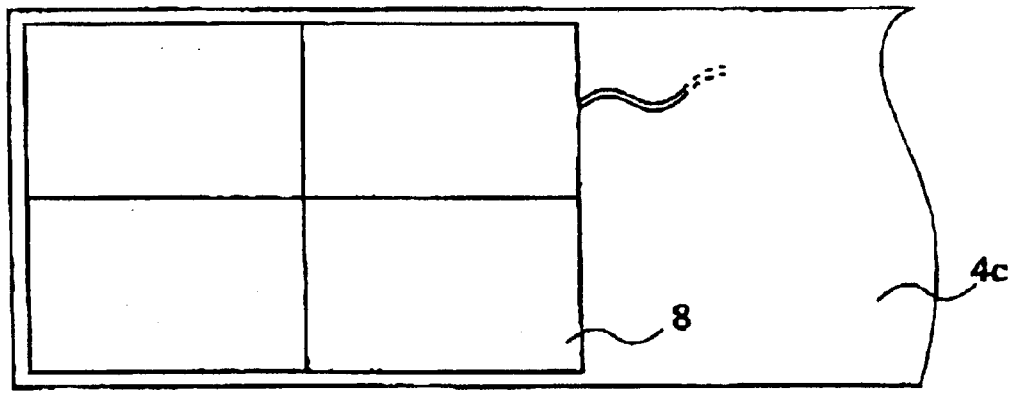
FIG. 3b shows the switching contact with piezoelectric element according to FIG. 3a as viewed in the direction of the arrow.

FIG. 1 shows a switching device according to the present invention in the form of a contactor. A contactor of that kind includes a multipart housing 2 in which are arranged a contact system (here three-pole), a magnetic drive 6 acting upon this contact system 4, as well as electronic and/or mechanical tripping elements.

AS1, AS2 and AS3 indicate positions at which acoustic device 8 for producing and capturing sound can be positioned in the switching device. Preferred positions for the attachment of the acoustic device include the positioning on contact piece carrier 4c, in particular, on the side diametrically opposite the contact piece 4d, or else, on the terminals of the switching device. In this manner, it is possible for sound waves to be injected directly into contact piece 4d itself, and for the reflected structure-borne sound waves to be captured and evaluated in an evaluation device.

FIGS. 2a and 2b are schematic views of a contact system 4 with appertaining magnetic drive 6. In this context, the contact system is essentially constituted by a movable switching contact 4a, here, in the form of a three-pole contact bridge which is driven via movable armature 6a of magnetic drive 6, and by stationary switching contacts 4b.

Moreover, the switching device according to the present invention has an evaluation unit, in particular, a microprocessor, for determining the remaining service life of the switching contacts. To this end, for example, reference values of different wear states are stored in the microprocessor, which are then compared to the measured actual values of the respective contact piece under examination, and a specific degree of wear is determined and assigned as a function thereof. In another embodiment, the degree of wear may be determined using a program which is stored in the processor, it being possible to determine a wear value by a certain algorithm. Subsequently, the determined degree of wear is interrogable via an interface (for example, using a PC or a diagnostic unit, or the like) or displayable at any time via an integrated displaying device.

The switching device according to the present invention includes acoustic devices 8 for producing and capturing structure-borne sound signals. These devices 8 advantageously include piezoelectric elements. These are piezoelectric elements which deliver precise signals over a wide range of high frequencies, preferably 20 kHz to 225 kHz or even 500 kHz.

Advantageously, both the device for producing structure-borne sound and the device for capturing structure-borne sound are combined in a single piezoelectric element. An acoustic device 8 designed in this manner is preferably arranged immediately opposite on contact piece carrier 4c. Structure-borne sound waves are injected into contact piece 4d using defined generation of structure-borne sound waves. Depending on the wear state of the contact piece, the sound waves are reflected to different degrees and a specific degree of wear is determined on the basis of the reflected structure-borne sound waves. This preferably takes place while the switching device is de-energized, in particular, while the switching contacts are open. In this manner, possible interference sources are eliminated from the start.

It is also possible for the producing and capturing devices to be formed separately. Thus, it is conceivable for the producing and capturing devices to be also arranged on the side of contact piece carrier 4c opposite an assigned contact piece 4d.

In a further embodiment, it is conceivable for interacting producing and capturing devices to be assigned to a contact pair and arranged on the outsides of the respective contact piece carriers 4c. In this arrangement, it would only be possible to determine the contact wear while the contacts are closed, structure-borne sound waves being injected in a defined degree on one side of the contact pair and captured on the other side of the contact pair. In this context, the intensity of the captured structure-borne sound waves is a measure for the wear of the contact pair.

As shown in FIG. 3a, such an acoustic device 8 can be arranged immediately on contact piece carrier 4c of the associated contact piece 4d. In a preferred embodiment of the present invention, the device which in each case is assigned to a switching contact is mounted in such a manner that a galvanic separation is assured. To this end, a ceramic carrier 4e is preferably mounted between contact piece carrier 4c and acoustic device 8. In this manner, a reliable galvanic separation is achieved without negatively influencing the capture of sound.

In a preferred embodiment, at least two devices 8 are assigned to one contact piece 4d. This makes it possible for a contact piece 4d to be examined in a partial and spatially resolved manner. This is an advantage since contact pieces 4d are generally subject to very irregular wear (erosion), and a qualitatively better determination of the condition of individual partial areas of contact piece 4d is made possible in this manner. For this embodiment, it is advantageous to arrange the individual device 8 on contact piece carrier 4c itself below the associated contact piece 4d on the side opposite the contact piece 4d. Advantageously, one contact piece 4d is assigned four devices 8. In this context, these are arranged, in particular, in such a manner that each device 8 covers one of four coordinate fields of a Cartesian coordinate system projected on contact piece 4d.

In another embodiment, a number of capturing devices (here piezos) assigned to a single contact piece 4d can be concentrically nested within one another. Thus, it is possible for circular and/or annular partial areas of a contact piece 4d to be evaluated in a differentiated manner. Depending on the application case, various other geometrical embodiments are conceivable as well.

To optimize the evaluation of the captured structure-borne sound waves, the individual devices 8, or the individual partial areas of a device 8 can be weighted differently. To this end, in one embodiment, provision is made for devices 8 of different sensitivity whereas in another embodiment, provision is made for identical or different devices 8, the captured signals of the individual devices 8 being weighted differently in the evaluation.

The present invention is not limited to the specific embodiments described above but is intended to be defined in scope by the appended claims. Advantageously, the evaluation device is, for example, integrated in the switching device. In another embodiment, however, the evaluation unit may be a separate device, it being possible to connect the switching device and the evaluation device via suitable standard interfaces. Moreover, the features shown in the drawing, including the geometry shown, belong to the present invention.

What is claimed is:

1. A system comprising:

a switching device, the switching device including a housing and a contact system disposed in the housing, the contact system including a contact piece carrier and a contact piece disposed on the contact piece carrier;

a sound device configured for producing and capturing structure-borne sound waves so as to determine an equivalent criterion useable for determining a remaining service life of the contact piece; and an evaluation device configured for evaluating the equivalent criterion.

2. The system as recited in claim 1 wherein the switching device is a low-voltage switching device.

3. The system as recited in claim 1 wherein the sound device includes a piezoelectric element.

4. The system as recited in claim 3 wherein the piezoelectric element is a high frequency piezoelectric element configured for a frequency range of from 20 kHz to 225 kHz.

5. The system as recited in claim 3 wherein the piezoelectric element is configured for producing and capturing structure-borne sound waves.

6. The system as recited in claim 1 wherein the sound device is disposed on the contact piece carrier immediately opposite the contact piece.

7. The system as recited in claim 1 wherein the sound device includes a first and a second sound device unit each assigned to a respective partial area of the contact piece.

8. The system as recited in claim 7 wherein the first and second sound device units are each assigned a respective weight for the evaluating the equivalent criterion.

9. The system as recited in claim 1 wherein the sound device includes a first, a second, a third and a fourth sound device unit assigned to the contact piece.

10. The system as recited in claim 9 wherein the first, the second, the third and the fourth sound device units are each formed in a respective quarter segment and are configured for imaging a respective equivalent criterion for wear of the contact piece over an entire geometrical extension of the contact piece in four respective individual coordinate areas.

11. The system as recited in claim 1 wherein the sound device includes an annular shape or a circular and annular shapes and is configured for imaging a wear of the contact piece over an entire geometrical extension of the contact piece.

12. The system as recited in claim 1 wherein the sound device is disposed on the contact piece carrier so as to assure a galvanic separation.

13. The system as recited in claim 1 further comprising a ceramic carrier disposed on the contact piece carrier and wherein the sound device is disposed on the ceramic carrier so as to assure a galvanic separation.

14. The system as recited in claim 1 wherein the evaluation device is integrated with the switching device.

15. The system as recited in claim 1 wherein the evaluation device is capable of being coupled to the switching device.

* * * * *